United States Patent [19]

Zaffaroni

[11] 4,014,989
[45] Mar. 29, 1977

[54] PHARMACEUTICAL AEROSOL COMPOSITIONS COMPRISING PUTRESCINE PROSTAGLANDINS

[75] Inventor: Alejandro Zaffaroni, Atherton, Calif.

[73] Assignee: Alza Corporation, Palo Alto, Calif.

[22] Filed: Oct. 1, 1975

[21] Appl. No.: 618,581

Related U.S. Application Data

[62] Division of Ser. No. 413,514, Nov. 7, 1973, abandoned, which is a division of Ser. No. 72,869, Sept. 16, 1970, Pat. No. 3,845,111.

[52] U.S. Cl. .................................. 424/45; 424/305; 424/316; 424/317
[51] Int. Cl.$^2$ ................. A61K 9/00; A61K 31/215; A61K 31/205
[58] Field of Search ............ 424/305, 317, 45, 316

[56] References Cited

UNITED STATES PATENTS

| | | | |
|---|---|---|---|
| 2,165,470 | 3/1939 | Fisk | 260/501.2 |
| 3,271,248 | 9/1966 | Renault et al. | 260/501.2 |
| 3,764,620 | 10/1973 | Zaffaroni | 260/501.2 |

FOREIGN PATENTS OR APPLICATIONS

| | | | |
|---|---|---|---|
| 481,036 | 12/1969 | Belgium | 260/501.2 |
| 1,120,243 | 7/1968 | United Kingdom | 260/501.2 |
| 1,040,544 | 9/1966 | United Kingdom | |
| 851,827 | 10/1960 | United Kingdom | |

Primary Examiner—Sam Rosen

Attorney, Agent, or Firm—Paul L. Sabatine; Steven D. Goldby

[57] ABSTRACT

Novel compounds of the formulae:

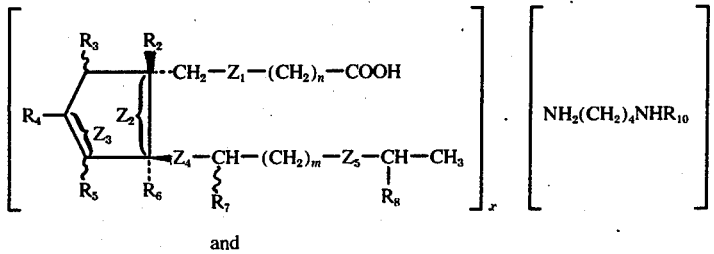

and

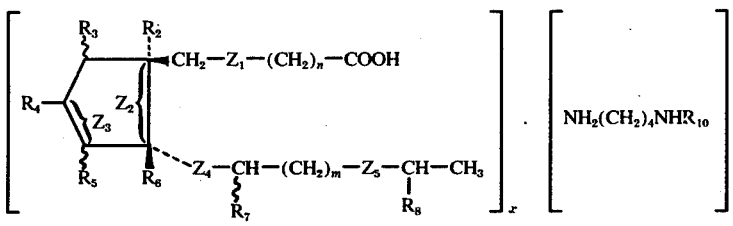

wherein $R_2$ and $R_6$ are hydrogen when $Z_2$ is a single bond and when $Z_2$ is a double bond $R_2$ and $R_6$ are absent; $R_3$ is a keto,

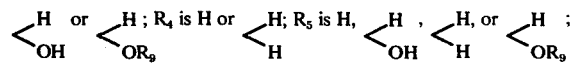

$R_7$ is OH or $OR_9$; $R_8$ is H or OH; $R_9$ is acyl or alkoxyalkyl; $R_{10}$ is H or

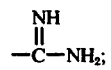

$Z_1$ is —$CH_2CH_2$— or cis —CH=CH—; $Z_2$ is a single bond or a double bond; $Z_3$ is a single bond or a double bond when $R_4$ and $R_5$ are hydrogen; $Z_4$ is —$CH_2CH_2$— or trans —CH=CH—; $Z_5$ is —$CH_2CH_2$— or cis —CH=CH—; $n$ is 2 to 5, $m$ is 1 to 3, and $x$ is 1 to 2. The compounds are useful for regulating blood pressure, for stimulating smooth muscles, for inhibiting gastric secretion and inhibiting platelet aggregation and they possess improved biological stability and enhanced membrane permeability to serve as an in vivo reservoir of the prostaglandin to ensure the biological availability of the prostaglandin.

1 Claim, No Drawings

PHARMACEUTICAL AEROSOL COMPOSITIONS COMPRISING PUTRESCINE PROSTAGLANDINS

CROSS REFERENCE TO RELATED APPLICATIONS

This application is a divisional of U.S. patent application Ser. No. 413,514 filed on Nov. 7, 1973 now abandoned which is a divisional of my copending U.S. patent application Ser. No. 72,869, filed on Sept. 16, 1970 now U.S. Pat. No. 3,845,111 issued on Oct. 29, 1974. Both of these applications are assigned to the same assignee.

BACKGROUND OF THE INVENTION

The present invention concerns new and useful compounds related to the prostaglandins. More particularly, the invention pertains to novel 1,4-diaminobutane prostaglandin compounds and to novel 1-amino-4-guanidobutane prostaglandin compounds that possess enhanced biological stability, and the property to perform as a pharmaceutical storage depot for eventual in vivo circulation of the 1,4-diaminobutane prostaglandins or 1-amino-4-guanidobutane prostaglandins to prostaglandin receptive sites whereupon the subsequent metabolic separation of the prostaglandin from the 1,4-diaminobutane or 1-amino-4-guanidobutane prostaglandin compound the valuable pharmacological properties of the parent prostaglandin are made available for performing its respective physiological function. The new 1,4-diaminobutane prostaglandins and 1-amino-4-guanidobutane prostaglandins of this invention have the structure as illustrated by Formulae I:

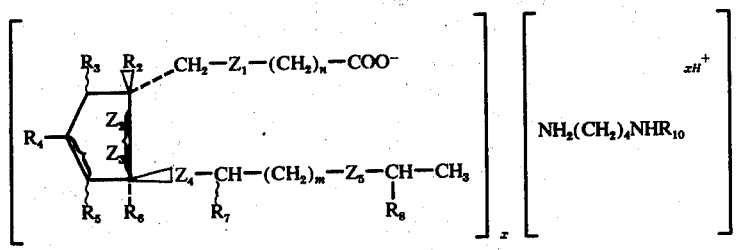

and

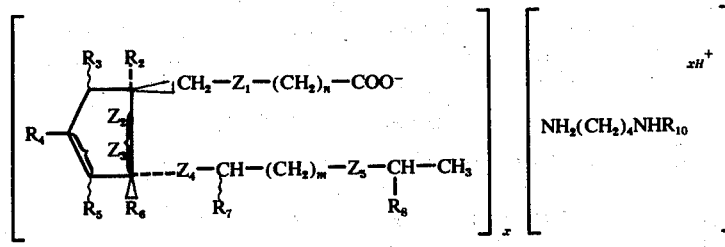

wherein $R_2$ and $R_6$ are hydrogen when $Z_2$ is a single covalent bond and $R_2$ and $R_6$ are absent when $Z_2$ is a double covalent bond; $R_3$ is a member selected from the group consisting of keto,

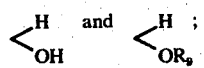

$R_4$ is selected from the group consisting of hydrogen and

$R_5$ is selected from the group consisting of hydrogen,

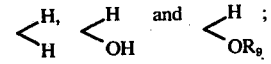

$R_6$ is hydrogen when $Z_2$ is a single bond and it is absent when $Z_2$ is a double bond; $R_7$ is selected from the group consisting of OH and $OR_9$; $R_8$ is selected from the group consisting of hydrogen and hydroxyl; $R_9$ is selected from the group consisting of acyl and alkoxyalkyl; $R_{10}$ is selected from the group consisting of hydrogen and $-C(:NH)NH_2$; $Z_1$ is selected from the group consisting of a saturated carbon carbon bond $-CH_2CH_2-$ and a cis unsaturated carbon carbon double bond $-CH=CH-$; $Z_2$ is selected from the group consisting of a single bond or a double bond; $Z_3$ is a single bond except when $R_4$ is hydrogen and $R_5$ is hydrogen and $R_4$ and $R_5$ are hydrogen $Z_3$ is a double bond; $Z_4$ is selected from the group consisting of a saturated carbon carbon bond $-CH_2CH_2-$ and a trans unsaturated carbon carbon bond $-CH=CH-$; $Z_5$ is selected from the group consisting of a saturated carbon carbon bond $-CH_2CH_2$ and a cis unsaturated carbon carbon double bond $-CH=CH-$; and wherein $n$ is 2 to 5, $m$ is 1 to 3 and $x$ is 1 to 2. The wavy line in the formula indicates the stereochemistry of the attached group on the cyclopentyl ring or on the side chain and it indicates either an $\alpha$ or $\beta$ configuration. The dotted line indicates that the attached group are $\alpha$ oriented or on the same side of the cyclopentyl ring as the carboxyl side chain and a wedged line indicates that the $\beta$-substituents are oriented on the same side of the ring as the alkyl side chain. The wavy line on the alkyl side chain indicates that the attached group may have a configuration represented by the terms sinister (S) and rectus (R) which for these compounds are equivalent nomenclature of α and β respectively.

The novel and the unobvious putrescine prostaglandins and agmatine prostaglandins of the invention as embraced by Formulae 1 are primarily related to the prostaglandins, a family of naturally occurring endogenous biologically important compounds possessing diverse and valuable pharmacological properties. The prostaglandins, a family of lipid acids are generally characterized as being 20 carbon atom prostanoic derivatives and they are usually separated into categories such as prostaglandin E, F, A and B. The separation of the prostaglandins depends on the arrangements of double bonds, hydroxyl and ketone groups, for example the E-type prostaglandins have an 11α-hydroxyl group and a 9-keto group in the five-membered cyclopentyl ring while in the F-type prostaglandins the 9-position is substituted with an α-hydroxyl group and the compound still retains the 11-hydroxyl group. The A-type and B-type prostaglandins do not have the familiar 11-hydroxyl group that is present in the E's and F's. The prostaglandins are also classified as primary, secondary and tertiary depending on the number of double bonds present in the prostaglandin. For example, the primary prostaglandins containing a 13:14 double bond are called $E_1$ and $F_1$. The prostaglandins that contain an additional double bond at the 5:6 position are designated as $E_2$ and $F_2$ and the prostaglandins with an added third double bond positioned at 17:18 are termed $E_3$ and $F_3$ respectively with the classification also used for the various categories.

The valuable physiological properties known by the art to be possessed by the prostaglandin family includes the prostaglandin ability to stimulate or control alimentary and reproductive smooth muscles, the ability to block gastric acid and enzyme secretions by the stomach, the property to stimulate the synthesis of adrenal corticoids, and to aid in regulating blood pressure, their possible role as a mediator of hormonal functions, and their ability to inhibit platelet aggregation. While the family as a group possesses these actions, the actions of each of the E, F, A and B prostaglandins are often dissimilar and sometimes they are opposed. For example, the prostaglandins of the E-type configuration are vasodepressors and they decrease the motility of the uterus at ovulation while the prostaglandins of the F-type usually have the opposite effects. The E-prostaglandins also inhibit platelet aggregation while the F-prostaglandins are devoid of this property. The prostaglandins of the A-type structure are like the E-type with respect to their vascular smooth muscle action but they possess a differing degree of relative potency as gastrointestinal secretion regulating agents.

Even though the prostaglandins are known to possess the above mentioned valuable pharmacological utilities in vitro that could be selectively used by various glands, tissues and organs, the potential pharmaceutical utilization of these compounds has not been presently realized in vivo because the prostaglandins lack the necessary biological stability that lends itself to therapeutic application of the prostaglandins. For example, the prostaglandins of the art known biologically active E-type chemical structure in the present of acidic conditions readily change to prostaglandins of the A-type structure that possess different biological activities, and the A-type prostaglandins under prolonged exposure to biological gastric acidic conditions isomerize to B-type prostaglandins. The prostaglandins that are known by the art to evidence widely different biological activities which make their physiological application seemingly more difficult and sometimes unpredictable in the face of these possible in vivo changes in chemical structure and physiological activities. These changes also lessen the availability of useful prostaglandin for in vivo use by changing useful prostaglandins that can be absorbed from the vascular system to inactive metabolic forms of the prostaglandins.

In the light of the above presentation, it will be easily appreciated by those versed in the art that a need exists for increasing the biological stability of the family of prostaglandins while essentially maintaining and readily making available to biological receptors the physiologically useful prostaglandins. It will also be appreciated that a need exists for providing new prostaglandin compounds that can serve as a reservoir of the prostaglandin per se for vascular circulation and subsequent availability by release of the prostaglandin from the prostaglandin compound to cells, glands and tissues for their immediate physiological use while simultaneously increasing the biological stability of the prostaglandin.

Accordingly, it is an immediate object of the present invention to make available to the art novel and unobvious prostaglandin compounds that overcome the problems often associated with the prior art.

Yet another object of the present invention is to provide new prostaglandin compounds that possess enhanced biological stability against rapid metabolism to ensure their in vivo employment for their known pharmacological properties.

Still yet another purpose of the subject invention is to provide prostaglandin compounds that can act as both an intracellular and extracellular biological reservoir of the prostaglandin for circulating within the vascular system to ensure increased availability as needed by the cells, glands and tissues for their immediate use.

Yet still another object of the invention is to provide prostaglandin compounds that possess enhanced cell membrane permeability in certain hosts for intracellular prostaglandin performance.

Another object of the invention is to provide new 4-(aminobutyl)guanidine prostaglandins and 1,4-diaminobutane prostaglandins that possess useful properties for both in vivo and in vitro applications.

These and other features, objects and advantages of the present invention will become more readily apparent from the following detailed description of the invention taken in conjunction with the accompanying claims.

SUMMARY OF THE INVENTION

The present invention concerns novel 4-(aminobutyl)-guanidine prostaglandins and 1,4-diaminobutane prostaglandins that are characterized by unobvious and desirable biological properties such as improved biological stability, the property of the 4-(aminobutyl)-guanidine prostaglandins on the 1,4-diaminobutane prostaglandins to circulate within the vascular system as a biological reservoir for a continual source of the prostaglandin moiety of the novel compounds at the needed biological prostaglandin receptive site following the release of the prostaglandin moiety from the compound, and also by an enhanced membrane permeability for absorption through the biological membranes.

DESCRIPTION OF THE INVENTION

The novel 4-(aminobutyl)-guanidine prostaglandins and 1,4-diaminobutane prostaglandins of the invention as illustrated by Formulae I are prepared by contacting and reacting a prostaglandin of Formulae II:

FORMULAE II

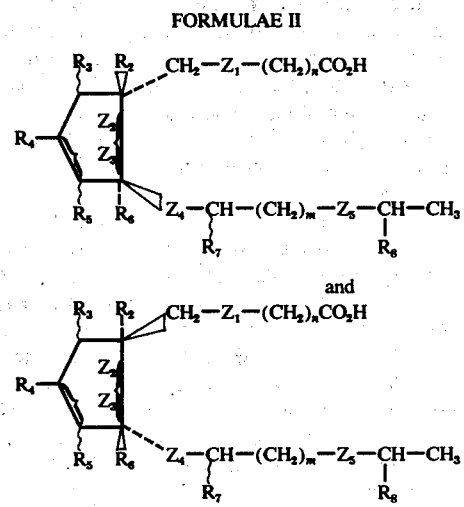

wherein $R_2$ and $R_6$ are hydrogen when $Z_2$ is a single bond and $R_2$ and $R_6$ are absent when $Z_2$ is a double bond; $R_3$ is keto,

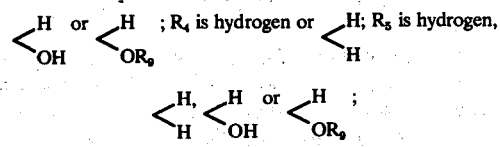

$R_7$ is hydroxy or $OR_9$; $R_8$ is hydrogen or hydroxy; $R_9$ is an acyl derived from a carboxylic acid or an α-alkoxy-alkyl; $Z_1$ is a saturated carbon carbon bond —$CH_2C$-$H_2$— or a cis unsaturated carbon carbon bond —$CH=CH$—; $Z_2$ is a single bond or a double bond; $Z_3$ is a single bond except when $R_4$ is hydrogen and $R_5$ is hydrogen and when $R_4$ and $R_5$ are hydrogen $Z_3$ is a double bond; $Z_4$ is a saturated carbon carbon bond —$CH_2CH_2$— or a trans unsaturated carbon carbon bond —$CH=CH$—; $Z_5$ is a saturated carbon carbon bond —$CH_2C$-$H_2$— or a cis unsaturated —$CH=CH$—; $n$ is 2 to 5; $m$ is 1 to 3.

The wavy line in the formula indicates the stereochemistry of the attached substitutents on the cycloalkyl ring or on the side chain may have either an α or a β configuration. The dotted line indicates that the attached groups are α-oriented or on the same side of the cyclopentyl ring or the carboxyl side chain and the wedged line indicates that the β-substituents are oriented on the same side of the ring as the alkyl side chain. The wavy line on the alkyl side chain indicates that the attached groups may have a configuration represented by the terms sinister (S) and rectus (R) which for these compounds are equivalent nomenclature of α and β respectively; with a compound of Formula III:

$NH_2(CH_2)_4NHR_{10}$ wherein $R_{10}$ is selected from the group consisting of hydrogen and

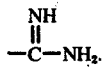

The reaction of the prostaglandins of Formulae II with either the 1,4-diaminobutane or the 4-(aminobutyl) guanidine of Formula III for preparing the corresponding prostaglandin compound of Formulae I is carried out in the presence of a suitable inert solvent with mixing of stoichiometric amounts of the reactants at room temperature or in a warmed solvent and gradually mixing the reacting ingredients until all the ingredients are in solution. The novel 1,4-diaminobutane prostaglandin or the 4-(aminobutyl) guanidine product is obtained by chilling the resulting mixture to precipitate the crystals, powder or the product that can be isolated by the addition of a miscible diluent of low polarity or by standard evaporation techniques. The obtained crystals or powders are filtered, washed and dried, usually in a desiccator over a known drying agent to a constant weight.

The starting materials used herein to synthesize the novel compounds of Formulae I are prepared in known ways or they are readily obtained from commercial sources. The reacting materials of Formulae II are easily prepared in art known ways either by isolating the prostaglandin from natural sources, for example, the vesicular glands of sheep, or by the enzymatic conversion from fatty acid substrates such as arachidonic acid, and depending on the substituents desired, routinely chemically transforming double bonds to single bonds by hydrogenation, converting keto groups to hydroxymethylene groups by reduction, by dehydrating to introduce double bonds, by forming carbinol derivatives by treating a carbo(lower) alkoxy group with an alkali metal alumino hydride reducing agent such as lithium aluminum hydride and the like. Specific prior art methods that set forth the procedures useful to provide all of the compounds of Formulae II are found in Science, Vol 158, pages 382 to 391, 1967; Recueil, Vol. 85, pages 1233 to 1250, 1966; Biochem. Biophys. Acta., Vol. 106, pages 215 to 217, 1965, Agnew. Chem. Inter. Ed., Vol. 4, pages 410 to 416, 1965; Experientia, Vol. 21, pages 113 to 176, 1965; Recueil, Vol. 85, pages 1251 to 1253, 1966 and other art recorded procedures.

The prostaglandin compounds depicted by Formulae II can also be chemically synthesized by well-known methods, for example, from 2-oxobicyclo-(3.3.0)-oct-6-en-3-one as described in Tetrahedron Letters, Vol. 4, pages 311 to 313, 1970; by the hydrogenation of 11,15-bis(tetrahydropyranyl) ether of 9α,11α,15(S)-trihydroxy-5-cis,13-trans-prostadienoic acid over Pd/C followed by hydrolysis and treatment with Jones reagent to give the resulting prostaglandin as reported in J. Am. Chem. Soc., Vol. 92, pages 2586 to 2587, 1970; by the acid-catalyzed opening and rearrangement of epoxybicyclo (3.1.0)-hexane as described in J. Am. Chem. Soc., Vol. 91, pages 5364 to 5371, 1969; by the reduction of 9-oxo and 15-oxo prostaglandin derivatives to give the R and S isomers of the corresponding hydroxyls and the dehydration of 11-hydroxy-9-oxoprostanoic acid to give the ketones as recorded in J. Org. Chem., Vol 34, pages 3552 to 3557, 1969; and J. Lipid Research, Vol 10, pages 320–325, 1969; as prepared by reduction of 2-oxo-3-oxo-6-exo-(trans-3-(S)hydroxyhept-1-enyl)-endo-7-acetoxy-cis-bicyclo(3.3.0)octane followed by reduction and treatment with Wittig reagent to give the corresponding prostaglandin as in *J. Am. Chem. Soc.*, Vol 91, pages 5675 to 5677, 1969; and other reported chemical synthesis embracing compounds within Formulae II such as *J. Am. Chem. Soc.*, Vol 92, pages 937 to 938, 1970; *J. Am. Chem. Soc.*, Vol 91, pages 5675 to 5677, 1969; *Tetrahedron Letters*, Vol 5, pages 465 to 470, 1966; *The Proceedings of the Robert A. Welch Foundation Conference on Chemical Research*, Vol XII, pages 51 to 79, 1969; *Chem. Abst.*, Vol 66, page 75770; and *Tetrahedron Letters*, No. 59, pages 5185–5188, 1969.

Representative of the alkanoyl moieties are the alkanoyl groups containing 1 to 18 carbon atoms such as formyl, acetyl propionyl, butyryl, isovaleryl, valeryl, hexanoyl, caproyl, octanoyl, heptanoyl, lauroyl, palmitoyl, stearoyl, nonanyl, oleoyl and the like. Exemplary of α-alkoxyalkyl groups embraced with $R_9$ is the group

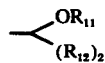

wherein $R_{11}$ is an alkyl group of 1 to 7 carbon atoms inclusive, such as the straight or branched chain alkyl groups methyl, ethyl, n-propyl, iso-propyl, n-butyl, tert-butyl, pentyl, neopentyl, n-hexyl, isohexyl and the like. The group $R_{12}$ is hydrogen or the lower alkyls of 1 to 7 carbon atoms as just set forth.

Compounds that are suitable for the purpose of the invention that are represented by Formulae II with their usual names based on art recognized prostanoic acid nomenclature and followed by the presently used abbreviations are the compounds 11α,15(S)-dihydroxy-9-oxo-13-trans-prostenoic acid($PGE_1$); 11β,15(R)-dihydroxy-9-oxo-13-trans-prostenoic acid,(11,15-epi-$PGE_1$); its antipodes, ent-11,15-epi-$PGE_1$; 11α,15(S)-dihydroxy-9-oxo-5-cis,13-trans-prostadienoic acid,($PGE_2$); 11α,15(S)-dihydroxy-9-oxo-5-cis,13-trans,17-cis-prostatrienoic acid,($PGE_3$); 15(S)-hydroxy-9-oxo-10,13-trans-prostadienoic acid, ($PGA_1$); 15(S)-hydroxy-9-oxo-5-cis,10,13-trans-prostatrienoic acid, ($PGA_2$); 9α,11α,15(S)-trihydroxy-13-trans-prostenoic acid, ($PGF_{1\alpha}$); 9β,11α,15(S)-trihydroxy-13-trans-prostenoic acid, ($PGF_{1\beta}$); 9β,11β,15(R)-trihydroxy-13-trans-prostenoic acid, (11,15-epi-$PGF_{1\beta}$); its antipode, ent-11,15-epi-$PGF_{1\beta}$; 9α,11α,15(S)-trihydroxy-5-cis,13-trans-prostadienoic acid, ($PGF_{2\alpha}$); 9β,11α,15(S)trihydroxy-5-cis,13-trans-prostadienoic acid, ($PGF_{2\beta}$); 9α,11α,15(S)-trihydroxy-5-cis,13-trans,17-cis-prostatrienoic acid, ($PGF_{3\alpha}$); 9β,11α,15(S)-trihydroxy-5-cis,13-trans-17-cis-prostatrienoic acid, ($PGF_{3\beta}$); 15(S)-hydroxy-9-oxo-8(12),13-trans-prostadienoic acid, ($PGB_1$); 15(S)-hydroxy-9-oxo-5-cis,8(12),13-trans-prostatrienoic acid, ($PGB_2$); 15(S),19-dihydroxy-9-oxo-8(12),13-trans-prostadienoic acid, (19-hydroxy $PGB_1$); 15(S)-19-hydroxy-9-oxo-10,13-trans-prostadienoic acid, (19-hydroxy $PGA_1$); 15(S)-hydroxy-9-oxo-8(12)-prostanoic acid, (dihydro $PGB_1$); and the like.

The starting material of Formula III, 1,4-diaminobutane, also known as tetramethylene diamine and putrescine, is a naturally occurring product formed in certain mammals on the decarboxylation of the amino acid ornithine by the enzyme ornithine decarboxylase. The compound is commercially available and it can also be synthesized according to the procedure of Japanese Pat. No. 158,357 by the ammonolysis of a saturated straight chain hydrocarbon dibromide in the presence of an aluminum catalysts to give the corresponding straight chain hydrocarbon diamine. The compound, 1,4-diaminobutane can also be prepared by the hydrogenation of 1,2-dicyanoethylene using a cobalt catalyst and ammonia as described in British Pat. No. 576,015. Other known procedures for the preparation of 1,4-diaminobutane include the benzoylation of a halobutylamine and then converting the monobenzoyl-halobutylamine with ammonia to the diaminobutane as in *Biochem. J.*, Vol 19, pages 845 to 849, 1925; and by the procedure in *Arch. of Biochem. and Biophys.*, Vol 79, pages 338 to 354, 1959.

The starting material of Formula III, 1-amino-4-guanidobutane, also known as 4-(aminobutyl)-guanidine and agmatine, occurs naturally in ergot, sponges and herring sperm and in certain mammals resulting from the decarboxylation of the exogenous essential amino acid arginine, α-amino-guanidinovaleric acid. Agmatine is commercially available and it can be synthesized from tetramethylene diamine by reacting it with silver cyanamide according to the procedure in *Z. Physiol. Chem.*, Vol 68, pages 170 to 172, 1910; *ibid*, Vol 118, pages 277 to 283, 1922. Agmatine can also be made by the $H_2NCN$ $H_2NC(:NH)SCH_3$ process of *J. Chem. Soc., Japan*, Vol 67, pages 132 to 133, 1946; and *Ber.*, Vol 90, pages 1251 to 1258, 1957. The starting reactants of Formulae II and Formula III used to synthesize the compounds of Formulae I are known to the art and these starting reactants are not part of the present invention.

The solvents suitable for the purposes of the present invention include the more polar type of solvents such as tetrahydrofuran, chloroform, acetone, methylene chloride, ethylene chloride, dioxane, isobutyl ketone, methyl isobutyl ketone, dimethyl ether, diethyl ether, alkanols such as methanol, methyl butanol, n-amyl alcohol, 2-ethyl hexyl alcohol, ethylene glycol, ethanol, isopropanol, hexanol, butanol, pentanol and lesser polar solvents such as benzene, carbon tetrachloride, cycloalkanes such as cyclopentane, 1,2-dimethylcyclopentane, cyclooctane, isopropylcyclohexane, cyclohexane, and methylcyclohexane; alkanes such as 3-methylpentane, n-hexane, n-heptane and the like.

The following examples are given simply to illustrate this invention, but they are not in any way to be construed as limiting the scope of the invention as these and other means for performing the invention will be obvious to those versed in the art in the light of this disclosure.

EXAMPLE 1

To a room temperature solution of 11α,15(S)-dihydroxy-9-oxo-13-trans-prostenoic acid (0.355 gram, 0.001 mole) in 100 milliters of dry methylene chloride there is added 0.130 gram, 0.001 mole of 1-amino-4-guanidobutane. The mixture is heated to about 35° C and cooled to room temperature. Then, 100 milliters of petroleum ether is added and the resulting mixture is chilled in an ice bath. The solids are filtered, washed with more petroleum ether and suspended in warm dry petroleum ether. Petroleum ether is added until turbidity develops and the mixture is chilled overnight. The crystals are filtered, washed with petroleum ether and dried in a desiccator over concentrated sulfuric acid to a constant weight, to give the novel compound 1- amino-4-guanidobutane 11α,15(S)-dihydroxy-9-oxo-13-trans-prostenoate.

EXAMPLE 2

To a room temperature 30 ml solution of ethanol containing 0.352 gram, 0.001 mole of 11α,15(S)-dihydroxy-9-oxo-5-cis-13-trans-prostadienoic acid is added with constant stirring a 30 ml of warmed, methanol solution of 0.130 gram, 0.001 mole of 1-amino-4-guanidobutane. Next, the solution is evaporated under vacuum and the resulting product is triturated with ether-benzene mixtures and the product 1-amino-4-guanidobutane 11α,15(S)-dihydroxy-9-oxo-5-cis-13-trans-prostadienoate is dried in a desiccator over concentrated sulfuric acid.

EXAMPLE 3

The procedure of Example 2 is employed in this example by reacting stoichiometrically equivalent amounts of 9α,11α,15(S)-trihydroxy-13-trans-prostenoic acid with 1-amino-4-guanidobutane in methylene chloride with constant stirring at room temperature. After the solution is evaporated under light in-house vacuum, the product 1-amino-4-guanidobutane 9α,11α,15(S)-tri-hydroxy-13-trans-prostenoate is triturated with dry cyclohexane and the product is filtered, washed with benzene; and, finally it is dried in a desiccator over concentrated sulfuric acid to a constant weight.

EXAMPLE 4

The synthesis of 1-amino-4-guanidobutane 9α,1-1α,15(S)-trihydroxy-5-cis,13-trans-prostadienoate is carried out by first adding to a room temperature 50 ml tetrahydrofuran solution containing 0.708 gram, 0.002 mole of 9α,11α,15(S)-trihydroxy-5-cis-13-trans-prostadienoic acid to a 50 ml tetrahydrofuran solution containing 0.260 gram, 0.002 mole of 1-amino-4-guanidobutane with constant stirring until the mixing of the two solutions is complete. Next, the mixed solution is warmed to about 50° C to 55° C for ½ to ¾ hours to ensure essentially complete formation of the desired product. Then, the solution is cooled to room temperature and the solvent evaporated with the resulting product triturated with dry benzene. Finally, the product is filtered, washed with a little benzene and dried in a vacuum desiccator to constant weight.

EXAMPLE 5

Preparation of 1,4-diaminobutane 11α,15(S)-dihydroxy-9-oxo-13-trans-prostenoate: To a room temperature solution of 0.355 gram of 11α,15(S)-dihydroxy-9-oxo-13-trans-prostenoic acid in 100 ml of dry ethylacetate is added 0.088 gram of 1,4-diaminobutane in 100 ml of dry benzene. Then, 0.2 liter of petroleum ether is added and the resulting mixture is chilled and the formed solids are filtered, washed with petroleum ether and suspended in warm dry benzene. Petroleum ether is again added until turbidity develops and the mixture is chilled overnight. The crystals are filtered, washed with petroleum ether and dried in a desiccator over concentrated sulfuric acid to a constant weight.

EXAMPLE 6

The synthesis of 1,4-diaminobutane bis-(9α,1-1α,15(S)-trihydroxy-13-trans-prostenoate) is carried out by first adding to a room temperature 50 ml tetrahydrofuran solution containing 0.712 gram, 0.002 mole of 9α,11α,15(S)-trihydroxy-13-trans-prostenoic a 50 ml tetrahydrofuran solution containing 0.088 gram, 0.001 mole of 1,4-diaminobutane with constant stirring until the mixture of the two solutions is complete. Next, the mixed solution is warmed to about 50° C to 55° C for ½ to 1½ hours to assure essentially complete formation of the desired product. Then, the solution is cooled to room temperature and the solvent evaporated with the resulting product triturated with mixtures of benzene petroleum ether. Finally, the product is filtered, washed with a little benzene and dried in a vacuum desiccator to a constant weight.

EXAMPLE 7

The compound 1,4-diaminobutane bis(-9α,1-1α,15(S)-trihydroxy-5-cis-13-trans-prostadienoate) is prepared by mixing 0.706 gram, 0.002 mole of 9α,1-1α,15(S)-trihydroxy-5-cis,13-trans-prostadienoic acid in 50 ml of dioxane with 0.088 gram, 0.001 mole of 1,4-diaminobutane in 50 ml of dioxane at room temperature. Next, the solution is heated to about 45° C to 50° C to assure the formation of the ionic compound 1,4-diaminobutane bis(-9α,11α,15(S)-trihydroxy-5-cis,13-trans-prostadienoate). Finally, the solvent is evaporated and the product triturated with benzene. The product is filtered, washed with a little benzene and dried in a vacuum desiccator to a constant weight.

EXAMPLE 8

The compound 1-amino-4-guanidobutane-bis-(11α,15(S)-dihydroxy-9-oxo-13-trans,prostenoate) is prepared by contacting and reacting (0.710 gram, 0.002 mole) of 11α,15(S)-dihydroxy-9-oxo-13-trans,-prostenoic acid in 50 ml of dioxane with 0.130 gram, 0.001 mole of 1-amino-4-guanidobutane in 50 ml of dioxane at room temperature. Next, the solution containing the two reactants is heated to about 45° C to 50° C to assure the formation of the ionic compound 1-amino-4-guanidobutane bis-(11α,15(S)-dihydroxy-9-oxo-13-trans,prostenoate). Finally, the solvent is evaporated and the product triturated with benzene. The product obtained is filtered, washed with a little benzene and dried in a vacuum desiccator to a constant weight.

Other novel compounds that are readily prepared according to the manner of the invention are for example, 1-amino-4-guanidobutane 11α,15(S)-dihydroxy-9-oxo-5-cis,13-trans,17-cis-prostatrienoate; 1-amino-4-guanidobutane 15(S)-hydroxy-9-oxo-10,13-trans-prostadienoate; 1-amino-4-guanidobutane 15(S)-hydroxy-9-oxo-5-cis,10,13-trans-prostatrienoate; 1-amino-4-guanidobutane 9β,11α,15(S)-trihydroxy-13-trans-prostenoate; 1-amino-4-guanidobutane 9β,11α,15(S)-trihydroxy-5-cis,13-trans-prostadienoate; 1-amino-4-guanidobutane 9α,11α,15(S)-trihydroxy-5-cis,13-trans,17-cis-prostatrienoate; 1-amino-4-guanidobutane 9β,11α,15(S)-trihydroxy-5-cis,13-trans-17-cis-prostatrienoate; 1-amino-4-guanidobutane 15(S)-hydroxy-9-oxo-8(12),13-trans-prostadienoate; 1-amino-4-guanidobutane 15(S)-hydroxy-9-oxo-5-cis,8(12),13-trans-prostatrienoate; 1-amino-4-guanidobutane 15(S),19-dihydroxy-9-oxo-8(12), 13-trans-prostadienoate; 1-amino-4-guanidobutane 15(S),19-dihydroxy-9-oxo-10,13-trans-prostadienoate; 1-amino-4-guanidobutane 11α,15(S)-dihydroxy-9-oxo-prostanoate; 1-amino-4-guanidobutane 15(S)-hydroxy-9-oxo-8(12)-prostanoate; 1,4-diaminobutane 11α,15(S)-dihydroxy-9-oxo-5-cis,13-trans-prostadienoate; 1,4- diaminobutane 11α,15(S)-dihydroxy-9-oxo-5-cis,13-trans,17-cis-prostatrienoate; 1,4-diaminobutane 15(S)-hydroxy-9-oxo-10.13-trans-prostadienoate; 1,4-diaminobutane 15(S)-hydroxy-9-oxo-5-cis,10,13-trans-prostatrienoate; 1,4-diaminobutane 9α,1-1α,15(S)-trihydroxy-13-trans-prostenoate; 1,4-diaminobutane 9β,11α,15(S)-trihydroxy-13-trans-prostenoate; 1,4-diaminobutane 9α,11α,15(S)-trihydroxy-5-cis,13-trans-prostadienoate; 1,4-diaminobutane 9α,11α,15(S)-trihydroxy-5-cis,13-trans-prostadienoate; 1,4-diaminobutane 9β,11α,15(S)-trihydroxy-5-cis,13-trans-prostadienoate; 1,4-diaminobutane 9α,11α,15(S)-trihydroxy-5-cis,13-trans,17-cis-prostatrienoate; 1,4-diaminobutane 9',11α,15(S)-trihydroxy-5-cis,13-trans-17-cis-prostatrienoic; 1,4-diaminobutane 15(S)-hydroxy-9-oxo-8(12),13-trans-prostadienoate; 1,4-diaminobutane 15(S),19-dihydroxy-9-oxo-10,13-trans-prostadienoate, 1,4-diaminobutane-bis-(11α,15(S)-dihydroxy-9-oxo-13-trans-prostenoate); 1,4-diaminobutane bis-(11α,15(S)-dihydroxy-9-oxo-5-cis,13-trans-prostadienoate; 1,4-diaminobutane bis-(11α,15(S)-dihydroxy-9-oxo-5-cis,13-trans,17-cis-prostatrienoate; 1,4-diaminobutane bis-(9β,11α,15(S)-trihydroxy-5-cis,13-trans-prostadienoate; 1,4-diaminobutane bis-(9α,11α,15(S)-trihydroxy-5-cis,13-trans,17-cis-prostatrienoate); 1,4-diaminobutane bis-(9β,11α,15(S)-trihydroxy-5-cis,13-trans-17-cis-prostatrienoate); 1,4-diaminobutane bis-(15(S),19-dihydroxy-9oxo-8(12),13-trans-prostadienoate and the like.

This invention resides in making available to the art the novel above described 1,4-diaminobutane prostaglandin compounds and 1-amino-4-guanidobutane prostaglandin compounds that are presently believed to possess unobvious and improved properties not suggested by the prior art such as enhanced stability towards biological conditions, the ability to act as an in vitro reservoir and thereby to serve as a source of prostaglandin per se when the 1,4-diaminobutane prostaglandins and 1-amino-4-guanidobutane prostaglandins are circulated by the vascular system to prostaglandin receptive sites in tissues, cells and the like, when in contact with the cellular membranes integral with the glands, tissues and cells, they may enter into the cell for subsequent metabolic hydrolysis of the novel 1,4-diaminobutane prostaglandin or 1-amino-4-guanidobutane to make available as the needed biological site prostaglandin per se. In addition, the compounds possess valuable properties that make them important for laboratory studies with laboratory animals because of their enhanced capillary permeability which makes possible topical absorption studies, cellular diffusion experiments, and the like.

The novel compounds of the invention can be used by the pharmaceutical and the veterinary arts in a variety of pharmaceutical preparations or veterinary preparations. In these preparations, the new compounds are administrable in the form of tablets, pills, powders, capsules, injectables, solutions, suppositories, emulsions, dispersions, food premix and in other suitable forms. The pharmaceutical or veterinary preparation which contains the compound is conveniently admixed with a non-toxic pharmaceutical organic carrier or a non-toxic pharmaceutical inorganic carrier. Typical of pharmaceutically acceptable carriers, are for example, water, gelatine, lactose, starches, magnesium stearate, talc, vegetable oils, polyalkylene glycols, petroleum jelly and other conventionally employed pharmaceutically acceptable carrier. The pharmaceutical preparation may also contain non-toxic auxiliary substances such as emulsifying, preserving, wetting agents and the like, as for example sorbitan monolaurate, triethanolamine oleate, polyoxyethylene sorbitan monopalmityl, dioctyl sodium sulfosuccinate, and the like.

Exemplary of a typical method for preparing a tablet containing the active ingredient is to first suitably comminute the active ingredient with a diluent such as starch, sucrose, kaolin or the like to form a powder mixture. Next, the just prepared mixture can be granulated by wetting with a non-toxic binder such as a solution of gelatin, acacial mucilage, corn syrup and the like and after mixing the composition is screened to any predetermined particle sieve size. As an alternative, if preferred, to granulation, the just prepared mixture can be slugged through conventional tablet machines and the slugs comminuted before the fabrication of the tablets. The freshly prepared tablets can be coated or they can be left uncoated. Representative of suitable coatings are the non-toxic coatings including shellac, methylcellulose, carnauba wax, styrene-maleic acid copolymers and the like. For oral administration, compressed tablets containing 0.1 milligram to 5 milligrams calculated as the free acid of the prostaglandins are manufactured in the light of the above disclosure and by art known fabrication techniques well known to the art and set forth in *Remington's Pharmaceutical Science*, Chapter 39, Mack Publishing Co., 1965.

The manufacture of capsules for oral use consists essentially of mixing the active compound with a non-toxic carrier and enclosing the mixture in a gelatin sheath. The capsules can be in the art known soft form of a capsule made by enclosing the compound in intimate dispersin within an edible oil or the capsule can be a hard capsule consisting essentially of the novel compound mixed with a non-toxic solid such as talc, calcium stearate, calcium carbonate or the like.

The daily dose administered for the compounds will of course vary with the particular novel compound employed because of the varying potency of the compounds, the chosen route of administration and the size of the recipient. The dosage administered is not subject to definite bounds, but it will usually be an effective amount of the pharmacologically active free acid form produced upon the metabolic release of the prostaglandin to achieve the biological function of the prostaglandin. Representative of a typical method for administering the putrescine or agmatine prostaglandin compounds is by the injectable-type administration route. By this route, a sterile solution containing the putrescine or agmatine prostglandin compound is administered intravenously at the rate of 0.01 microgram to 0.15 microgram per minute per kilogram of body weight by means of an infusion pump, at the rate of 10 to 15 milliliter per hour. For example, the compound 1-amino-4-guanidobutane 9α,11α,15(S)-trihydroxy-13-trans-prostenoate can be administered by this route for producing stimulation of smooth muscles. The compound is administered by the injectable route in a form suited for injection, such as mixed with sterile physiological saline, or in aqueous solutions having incorporated therein an agent that delays absorption such as aluminum monostearate and the like.

Suitable topical preparations can easily be prepared by, for example, mixing 500 mg of the putrescine or agmatine prostaglandin with 15 g of cetyl alcohol, 1g of sodium lauryl sulfate, 40 g of liquid silicone D.C. 200

Dow Corning, 43 g of sterile water, 0.25 g of methylparaben and 0.15 g of propylparaben and warming the mixture with constant stirring to about 75° C and then permitting the preparation to congeal. The preparation can be readily applied to the skin by inunction or it can be applied topically by dispensing the preparation from a conventional surgical gauze dispenser, and the like. Suitable procedures for preparing topical applications are set forth in *Remington's Pharmaceutical Science*, Chapter 37, as cited supra.

The compounds of this invention can also be conveniently administered in aerosol dosage form. An aerosol form can be described as a self-contained sprayable product in which the propellant force is supplied by a liquified gas. For administering a self-propelled dosage form of about 100 mg to 500 mg that is used about 3 or 4 times daily for inhalation therapy, the broncho-dialator 1,4-diaminobutane-11$\alpha$,15(S)-dihydroxy-9-oxo-5-cis,13-trans-prostadienoate is suspended in an inert non-toxic propellant in a commercially available compressed-gas aerosol container. Suitable propellants include trichloromonofluoromethane, dichlorodifluoromethane, dichlorofluoroethane, monochlorodifluoroethane and mixtures thereof. The inert gas can also be mixed with non-toxic cosolvents such as ethenol, if desired, to produce the aerosol form. If the compound is administered by oral inhalation employing conventional nebulizers, it is convenient to dilute in an aqueous solution about 1 part of the putrescine or agmatine prostaglandin with about 200 to 300 parts of solution, for administering 3 or 4 times per day.

For administering to valuable domestic animals or for administering to laboratory animals for scientific studies, the compound is prepared in the form of a food premix, such as mixing with dried fish meal, oatmeal and the like, and then the prepared premix is added to the regular feed, thereby administering the compound to the domestic or laboratory animal in the form of feed.

The above examples and disclosures are set forth merely for illustrating the mode and the manner of the invention and various modifications and embodiments can be made by those skilled in the art in the light of the invention without departing from the spirit of the invention.

I claim:

1. A pharmaceutical aerosol formation for inhalation therapy wherein the aerosol is comprised of about 100 mg to 500 mg of a prostonate selected from the group consisting of 1,4-diaminobutane-11$\alpha$,15(S)-dihydroxy-9-oxo-5-cis,13-trans-prostadienoate; 15(S)-hydroxy-9-oxo-10,13-trans-prostadienoate; 9$\alpha$,11$\alpha$,15(S)-trihydroxy-5-cis,13-trans-prostadienoate; and 9$\alpha$,11$\alpha$,15(S)-trihydroxy-5-cis,13-trans,17-cis-prostatrienoate wherein the prostonate is mixed with an inert non-toxic gaseous propellant and a pharmaceutically acceptable cosolvent for the propellant and the prostonate.

* * * * *